United States Patent [19]

Eguchi

[11] 4,081,485
[45] Mar. 28, 1978

[54] HYDROQUINONE-KETONE MOLECULAR COMPOUND AND PROCESS FOR PURIFYING HYDROQUINONE USING SAID MOLECULAR COMPOUND

[76] Inventor: Tsukasa Eguchi, 2-9-506, Akabanedai 1-chome, Kita, Tokyo, Japan

[21] Appl. No.: 755,101

[22] Filed: Dec. 28, 1976

[30] Foreign Application Priority Data

Jan. 1, 1976   Japan ................................. 51-332
Jan. 19, 1976  Japan ................................. 51-4046

[51] Int. Cl.$^2$ ............................................ C07C 39/02
[52] U.S. Cl. .............................. 260/621 A; 260/593 R
[58] Field of Search ........................... 260/396, 621 A

[56] References Cited

PUBLICATIONS

Heunisch et al., Chem. Abst., vol. 76, p. 311, #45292g (1972).
Lee et al., Chem. Abst., vol. 53, #9773f (1959).
Schmidlin et al., Chem. Ber., vol. 43, pp. 2806–2820 (1910).

Primary Examiner—James O. Thomas, Jr.
Assistant Examiner—James H. Reamer
Attorney, Agent, or Firm—Fred Philpitt

[57] ABSTRACT

The present invention relates to a novel compound which is considered to be a hydroquinone-ketone molecular compound. The invention also pertains to the method of producing such molecular compounds from hydroquinone and ketone. When the molecular compound is decomposed in the presence of water or an aqueous medium, hydroquinone can be obtained which undergoes little or no coloring even if left standing in the air for a prolonged period of time.

1 Claim, 2 Drawing Figures

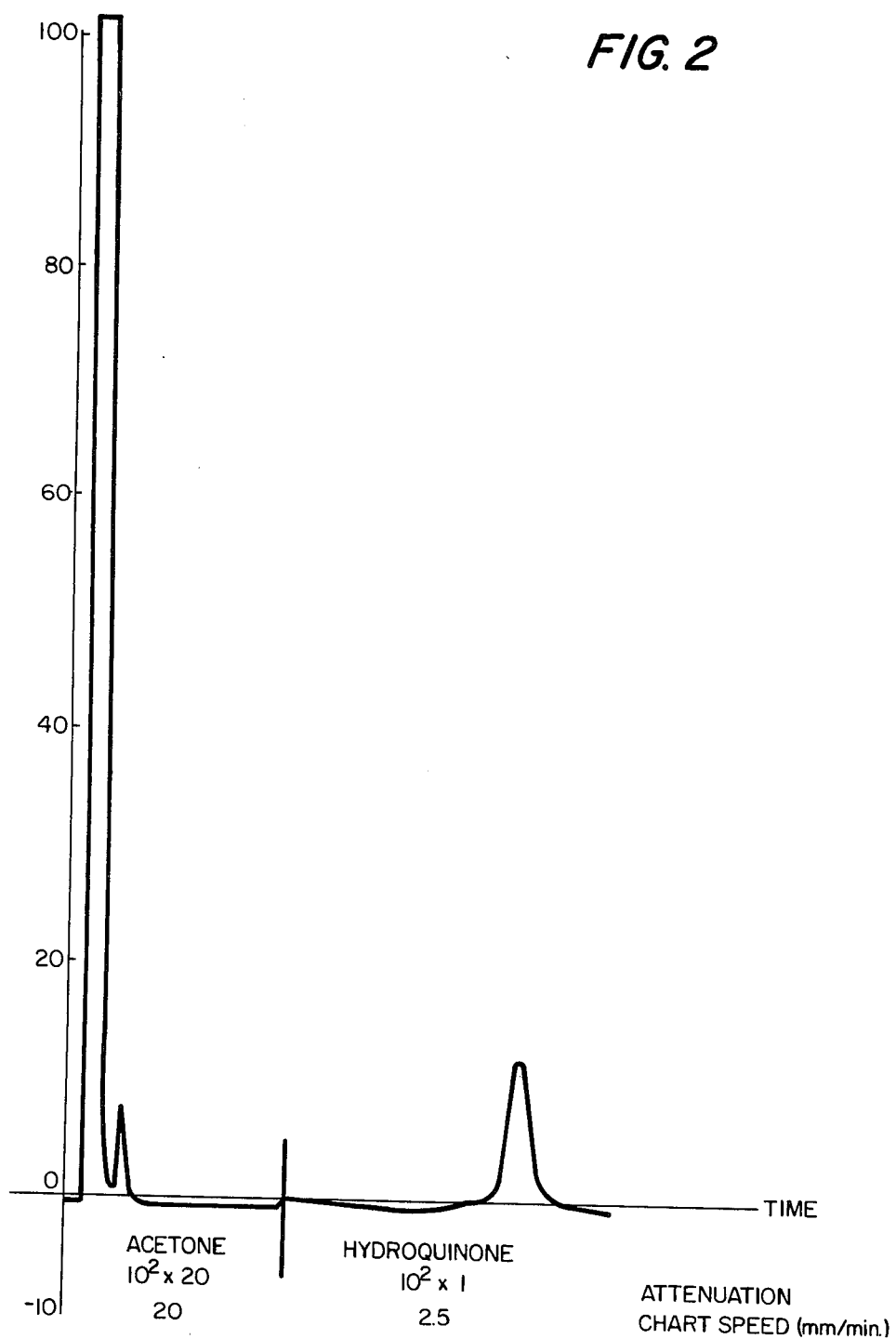

HYDROQUINONE-KETONE MOLECULAR COMPOUND AND PROCESS FOR PURIFYING HYDROQUINONE USING SAID MOLECULAR COMPOUND

BACKGROUND

It is well known that hydroquinone is generally purified by extraction and recrystallization, is composed of colorless needle or prismatic crystals, has a melting point of 169° C, has a boiling point of 287° C/73 mm Hg, sublimes at 285° C without decomposition, is soluble in water, ethanol and ether, and is sparingly soluble in cold benzene. Hydroquinone is used as a photographic developing agent, as an intermediate for dyes, organic synthesis, and medicine, or as an oxidation or polymerization inhibitor.

Even when crude hydroquinone, obtained by decomposing p-dialkylbenzene-bis-hydroperoxide (for example, p-diisopropylbenzene-bis-hydroperoxide, p-di-sec. butylbenzene-bis-hydroperoxide, etc.) in an acid medium is purified, utilizing said properties of hydroquinone, for example by recrystallization from water, the resulting purified hydroquinone undergoes coloring or discoloring to a light pink, etc. at least for about one week after the purification, even if the purification is carried out satisfactorily. This may lower the usefulness and value of the hydroquinone when it is used for certain applications, and especially when developing an important photographic picture which cannot be taken again. As a consequence, hydroquine is sometimes not used because of the uncertainties about the possible adverse effects of its occassional undesirable properties.

Therefore, it is very important from the standpoint of product value and reliability to insure that there will be no coloring or discoloring of the hydroquinone and that the hydroquinone will always be in the form of colorless crystals. In the production of hydroquinone, especially according to the cumene process, considerable coloring of the product takes place. For example, the hydroquinone in the decomposition product solution resulting from the decomposition of p-dialkylbenzene-bis-hydroperoxide in an acidic medium undergoes rapid change, especially in the presence of impurities, turning the product to a dark color. It is difficult to obtain a product that can meet the color requirements and other standards of the ASA (American Standards Association) relative to photographic materials, even though it is recrystallized from water. In order to solve this problem it has been proposed to add p-dialkylbenzene-bis-hydroperoxide to a mixture consisting of (a) an aromatic hydrocarbon, non-aqueous solvent capable of dissolving by-products formed in the course of the decomposition, but which is incapable of dissolving hydroquinone formed, and (b) an acid catalyst and dissolving the impurities during the decomposition and suppressing side reactions of hydroquinone with the impurities throughout the entire process of forming the hydroquinone, while placing the hydroquinone outside the solvent, and recovering the hydroquinone insoluble in the aromatic hydrocarbon solvent from said solvent by a mechanical means such as filtration (see Japanese Patent Publication No. 1538/1967).

It is well known, as described above, that it is difficult to improve the hydroquinone of not-so-good quality itself up to the desired quality even by the recrystallization of the hydroquinone from water, etc. Furthermore, it is difficult to completely prevent the coloring or discoloring of the hydroquinone in spite of the fact that the hydroquinone produced according to the cumene process is properly colorless, even though the said prior art process should be carried out. Thus, it is obviously very preferable in view of the product value to prevent the coloring or discoloring completely.

THE PRESENT INVENTION

According to the present invention it has found that hydroquinone can be formed into a "molecular compound" with a dialkylketone such as acetone, methylethylketone, or the like. When an equimolar amount of the ketone is added to hydroquinone, heated to the boiling point of the ketone, and cooled, crystals which are believed to be hydroquinone-ketone molecular compounds are obtained. When greater than an equimolar amount of the ketone is used, a mixture of crystals of said molecular compound and the excessive ketone is obtained. By filtering the mixture, crystals of the molecular compound can be separated from the excessive ketone.

My hydroquinone-ketone molecular compound has a crystal form similar to that of hydroquinone, and when the crystals are left standing in the air, ketone molecules such as acetone, methylethylketone, etc., vaporize off, even at room temperature, leaving a porous hydroquinone single compound standing in the air, which will become colored with time. Therefore, it is desirable to keep the temperature of the molecular compound below room temperature, preferably at a temperature of about −15° C. When the hydroquinone-acetone molecular compound is dried at a low temperature and left standing at the room temperature, the following change in weight with time is observable. It can be seen from the result of the weight reduction that hydroquinone (M.W. 110) and acetone (M.W. 58) are combined in a molar ration of 1.00:0.97 in the hydroquinone-acetone molecular compound.

| Date of Measurement | | Weight (mg) |
|---|---|---|
| Dec. 18 | 3:45 p.m. | 213 |
| " | 4:10 p.m. | 207 |
| " | 5:10 p.m. | 189 |
| " | 5:45 p.m. | 180 |
| Dec. 19 | 10:10 a.m. | 141 |
| Dec. 22 | 12:00 a.m. | 141 |

FIG. 2 shows results of measuring gas chromatography of the present hydroquinone-acetone molecular compound.

Figure 1:
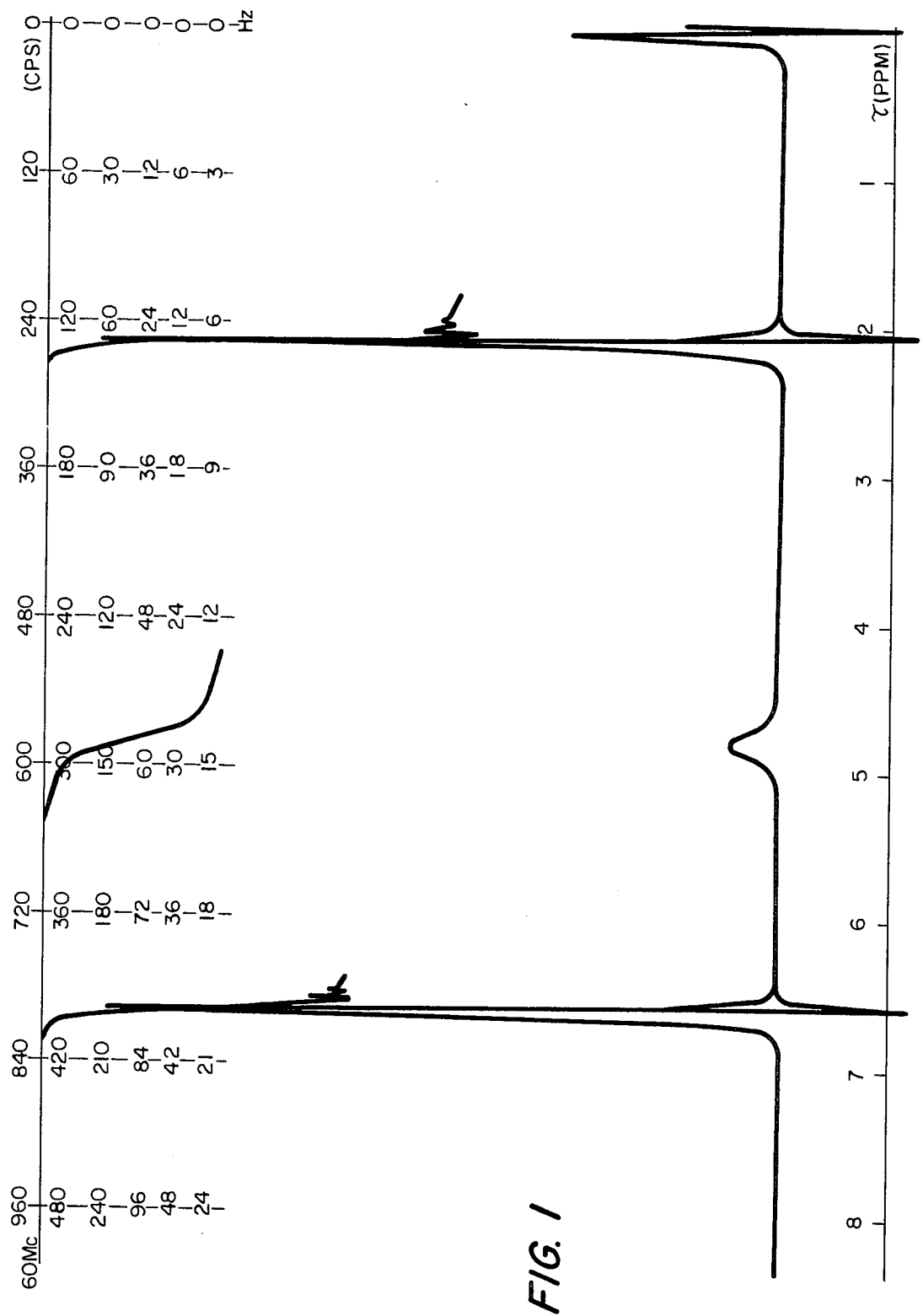
FIG. 1 shows results of measuring nuclear magnetic resonance spectra of the present hydroquinone-acetone molecular compound.

As shown in FIG. 1, it is seen from ratios of hydrogen numbers of the hydroquinone parts to acetone parts obtained by measuring the nuclear magnetic resonance spectra of the hydroquinone-acetone molecular compounds that hydroquinone and acetone are combined together at a molar ratio of 1.0: about 0.9 to form the molecular compound. Furthermore, as shown in FIG. 2, it is seen from the results of measuring the gas chromatography of the molecular compound that hydroquinone and acetone are combined together in a molar ratio of 1.0:1.04 to form the molecular compound. The values of the latter gas chromatography are obtained by measuring gas chromatographies of hydroquinone and acetone as standard samples, thereby preparing calibration curves, determining concentrations of hydroquinone and acetone, respectively, in a sample solution of the methanol-washed molecular compound in methanol by means of said calibration curves, and calculating their combining ratio from the concentrations as an average of eight samples. In view of measurement errors, the foregoing results of measurements reveals that hydroquinone and acetone are combined together at a molar ratio of 1:1 in the hydroquinone-acetone molecular compound.

I have found a process for purifying hydroquinone by utilizing my hydroquinone-ketone molecular compound effectively to such a good purity that even when the crystals of hydroquinone are left standing in the air for a prolonged period of time, they will not undergo coloring or discoloring.

One object of the present invention is to provide a novel hydroquinone-ketone molecular compound.

Another object of the present invention is to provide a hydroquinone-ketone molecular compound effectively applicable to the purification of hydroquinone.

Another object of the present invention is to provide a process for purifying hydroquinone, using the hydroquinone-ketone molecular compound as an intermediate for purification.

Still another object of the present invention is to provide crystals of hydroquinone which have little or no color even if left standing in the air for a prolonged period of time.

Purification of hydroquinone by utilizing my hydroquinone-ketone molecular compound is carried out by adding an equimolar or greater amount of ketone to hydroquinone, thereby forming a hydroquinone-ketone molecular compound, decomposing this molecular compound in the presence of water of an aqueous medium, and recovering essentially pure crystals of hydroquinone.

As mentioned above, my hydroquinone-ketone molecular compounds are unstable at room temperature, and thus are preferably kept at a temperature of about $-15°$ C or less. Generally, however, my molecular compounds formed from hydroquinone and ketone are immediately added to water or to an aqueous medium, heated, and cooled, whereby the ketone forming the molecular compound is separated from the molecular compound in water or the aqueous medium, and the hydroquinone then crystallized in the water-ketone mixed solvent.

Beside water, an organic solvent miscible with water, typically ketones (for example, dialkylketones such as acetone, methylethylketone, etc) can be used in a mixture with water as the aqueous medium. Water, which can be applied alone or in a mixture with the organic solvent, is usually used in an amount which is substantially equal to that of the ketone combined in the molecular compound in the present invention. The aqueous medium solution to which the molecular compound has been added is adjusted to an acidic condition, usually by adding an inorganic acid such as dilute sulfuric acid to make a pH of the medium solution about 1 to 5, preferably about 1.5 to 3.0, and then admixed with sulfurous acid or its alkali metal salt, and if necessary, a reducing and stabilizing material such as zinc powders, tin powders, iron powders, etc., at ratios by weight to the hydroquinone of 1/1000 or more, preferably 1/500 or more, respectively, and, if necessary, further admixed with an organic acid such as ascorbic, etc. to adjust the pH. Then, the aqueous medium solution is stirred at room temperature, or preferably heated up to the boiling point of the aqueous medium solution. The metallic powders, when used, are filtered off while hot, and then the aqueous medium solution is cooled down to room temperature, whereby crystals of hydroquinone crystallize out. The crystals are filtered off from the aqueous medium solution. The crystals of hydroquinone, which are substantially quantitatively obtained, are desirably dried at a relatively low temperature for a short period of time. Thus, it is preferable to dry the crystals in an inert gas atmosphere under as great a reduced pressure as possible.

The crystals of hydroquinone thus obtained do not have a porous crystal form, but are in a colorless needle or prismatic crystal form and undergo no coloring or discoloring with time, even if they are kept at the room temperature of a prolonged period of time.

The fact that hydroquinone produced according to the cumene process is formed into a hydroquinone-ketone molecular compound, and the resulting molecular compound is immediately decomposed with water, whereby hydroquinone having a good quality is obtained, is quite significant in comparison to said prior art processes, that is the disclosure that whether or not water is separable from a solvent containing hydroquinone in a suspended state is a key to the prevention of hydroquinone from becoming brown-colored, and ultimately the presence of water has an adverse effect upon the characteristics of hydroquinone, and consequently it is preferable to avoid the presence of water, and the disclosure that when the decomposition reaction of the cumene process is carried out in the presence of only ketone, the reaction mixture is considerably colored brown, and, in that case, the dark brown, semi-solid product resulting from evaporation of the solvent is intensely colored which is not removed completely even after washing with an aromatic hydrocarbon solvent, and thus the crude hydroquinone is hardly purified, etc.

The present process for purifying hydroquinone through the formation of a hydroquinone-ketone "molecular compound" provides hydroquinone having a distinguishable crystal form, which is colorless and resists coloring or discoloring, which means that the crystals of hydroquinone thus obtained can be safely and effectively utilized in a variety of applications.

The present invention will be illustrated in the following examples, but it will be understood that the invention is not limited to these examples or the details therein.

EXAMPLE 1

A mixture of 2 moles each of (a) purified, colorless hydroquinone and (b) acetone was heated up to the boiling point of acetone, then cooled to room temperature, and filtered. Crystals that were substantially quantitatively obtained had crystal forms similar to that of hydroquinone, and it was found from results of measuring reduction in weight by leaving the molecular compounds standing at room temperature, ratios of hydrogen numbers of hydroquinone molecular parts to acetone molecular parts obtained by measuring their nuclear magnetic resonance spectra (in heavy hydrogen methanol solvent) and their gas chromatography as described above, that the crystals were "molecular compounds" having a molar ratio of hydroquinone to acetone of substantially 1:1.

The resulting hydroquinone-acetone molecular compounds were immediately added to almost equal weight (120 g) of water to that of the combined acetone, admixed with dilute sulfuric acid to produce a pH of 2.0, then with 100 mg of sodium sulfite, heated until the solution was boiled, and then cooled to the room temperature. In that case, only stirring the solution at the room temperature in place of the heating will do.

Crystals of hydroquinone having the crystal form and melting point proper to hydroquinone were obtained, dried at 40° C under a reduced pressure in a nitrogen gas stream, and then the dried crystals were placed in a polyethylene bag. No coloring was observed when examined after two years.

EXAMPLE 2

Cumene process hydroquinone, which was purified by recrystallization from water, and which became pink-colored about one week after the recrystallization, was used in place of the hydroquinone of Example 1, and hydroquinone-acetone molecular compounds were prepared in the same manner as in Example 1. It was found from measuring reduction in weight by leaving the molecular compound standing at the room temperature, by their nuclear magnetic resonance spectra and by gas chromatography that they were molecular compounds having a molar ratio of hydroquinone to acetone of substantially 1:1.

Decomposition of the resulting hydroquinone-acetone molecular compounds by water was carried out in the same manner as in Example 1, whereby crystals of hydroquinone having a quality as good as that of the purified hydroquinone obtained in Example 1 were obtained.

EXAMPLE 3

Hydroquinone which had become pink-colored by leaving it standing in the air after the reduction in weight was measured by leaving the hydroquinone-acetone molecular compound standing in the air in Example 1 was used for repurification by producing a "molecular compound" in the same manner as described in Example 1. Crystals of hydroquinone having a quality as good as that obtained in Example 1 were obtained. Even when the crystals were left standing in the air for a prolonged period of time, no coloring was observed.

EXAMPLE 4

Purification of hydroquinone was carried out in the same manner as in Examples 1 and 2, except that methylethylketone was used in place of acetone. Crystals of hydroquinone having a quality as good as those obtained in Examples 1 and 2 were obtained in these cases.

What is claimed is:

1. A process for purifying hydroquinone which comprises
    (a) adding at least an equimolar amount of acetone to hydroquinone and heating the resulting mixture to the boiling point of acetone, thereby forming a hydroquinone-acetone molecular compound,
    (b) adding said molecular compound to water,
    (c) acidifying the resulting aqueous medium solution with sulfuric acid to a pH of about 1 to 5, and
    (d) treating the acidic medium solution in the presence of sodium sulfite at a temperature of between the room temperature and the boiling point of the acidic medium solution, thereby recovering crystals of hydroquinone.

* * * * *